United States Patent
Bengtsson

(10) Patent No.: US 10,946,130 B2
(45) Date of Patent: Mar. 16, 2021

(54) APPARATUS FOR PERFORMING PERITONEAL ULTRAFILTRATION

(71) Applicant: TRIOMED AB, Lund (SE)

(72) Inventor: Hans Bengtsson, Eslöv (SE)

(73) Assignee: TRIOMED AB, Lund (SE)

( * ) Notice: Subject to any disclaimer, the term of this patent is extended or adjusted under 35 U.S.C. 154(b) by 300 days.

(21) Appl. No.: 15/755,472

(22) PCT Filed: Aug. 26, 2016

(86) PCT No.: PCT/SE2016/000043
§ 371 (c)(1),
(2) Date: Feb. 26, 2018

(87) PCT Pub. No.: WO2017/034452
PCT Pub. Date: Mar. 2, 2017

(65) Prior Publication Data
US 2018/0169318 A1    Jun. 21, 2018

(30) Foreign Application Priority Data

Aug. 27, 2015   (SE) .................................... 1530127-8

(51) Int. Cl.
*A61M 1/28*   (2006.01)

(52) U.S. Cl.
CPC ............ *A61M 1/287* (2013.01); *A61M 1/281* (2014.02); *A61M 1/282* (2014.02); *A61M 1/285* (2013.01); *A61M 2210/1017* (2013.01)

(58) Field of Classification Search
CPC ...... A61M 1/287; A61M 1/281; A61M 1/282; A61M 1/284; A61M 1/285
See application file for complete search history.

(56) References Cited

U.S. PATENT DOCUMENTS 4,618,343 A * 10/1986 Polaschegg ............ A61M 1/28
                                                      210/321.65
5,141,493 A    8/1992 Jacobsen et al.
(Continued)

FOREIGN PATENT DOCUMENTS

EP    0 402 505 A1    12/1990
EP    0 498 382 A1    8/1992
(Continued)

*Primary Examiner* — Rebecca E Eisenberg
*Assistant Examiner* — John A Doubrava
(74) *Attorney, Agent, or Firm* — Birch, Stewart, Kolasch & Birch, LLP

(57) ABSTRACT

An apparatus for ultrafiltration of a patient being overhydrated due to congestive heart failure. The apparatus comprises a dilution syringe for removal of a portion of peritoneal fluid from the peritoneal cavity. A glucose bag comprises glucose concentrate at a concentration of 30%. A small amount of glucose concentrate is mixed with the dilution fluid in the dilution syringe in order to dilute the glucose concentrate to below 3% concentration. Then, the mixture is filled into the peritoneal cavity from the dilution syringe in order to replenish the glucose in the peritoneal cavity for maintaining a substantially constant glucose concentration in the peritoneal cavity. In addition, peritoneal fluid is intermittently removed from the peritoneal cavity for counteracting increased intraperitoneal fluid volume and increased intraperitoneal pressure due to ultrafiltration. A UF bag is arranged for receiving such surplus peritoneal fluid. A glucose syringe may be arranged for metering the glucose concentrate.

12 Claims, 10 Drawing Sheets

(56) References Cited

U.S. PATENT DOCUMENTS

| | | | |
|---|---|---|---|
| 5,944,684 | A | 8/1999 | Roberts et al. |
| 6,228,047 | B1 | 5/2001 | Dadson |
| 7,135,008 | B2 | 11/2006 | O'Mahony et al. |
| 9,242,035 | B2 | 1/2016 | Karoor |
| 2002/0162778 | A1 | 11/2002 | Peabody et al. |
| 2005/0234392 | A1 | 10/2005 | Mineshima et al. |
| 2007/0179431 | A1 | 8/2007 | Roberts et al. |
| 2007/0213665 | A1 | 9/2007 | Curtin et al. |
| 2008/0051696 | A1 | 2/2008 | Curtin et al. |
| 2010/0312174 | A1 | 12/2010 | Hoffman |
| 2011/0105981 | A1 | 5/2011 | Wagner et al. |
| 2012/0230844 | A1 | 9/2012 | Farrell et al. |
| 2014/0018727 | A1 | 1/2014 | Burbank et al. |

FOREIGN PATENT DOCUMENTS

| | | |
|---|---|---|
| GB | 1 462 349 A | 1/1977 |
| WO | WO 95/35124 A1 | 12/1995 |
| WO | WO 00/57935 A1 | 10/2000 |
| WO | WO 2015/130205 A1 | 9/2015 |

\* cited by examiner

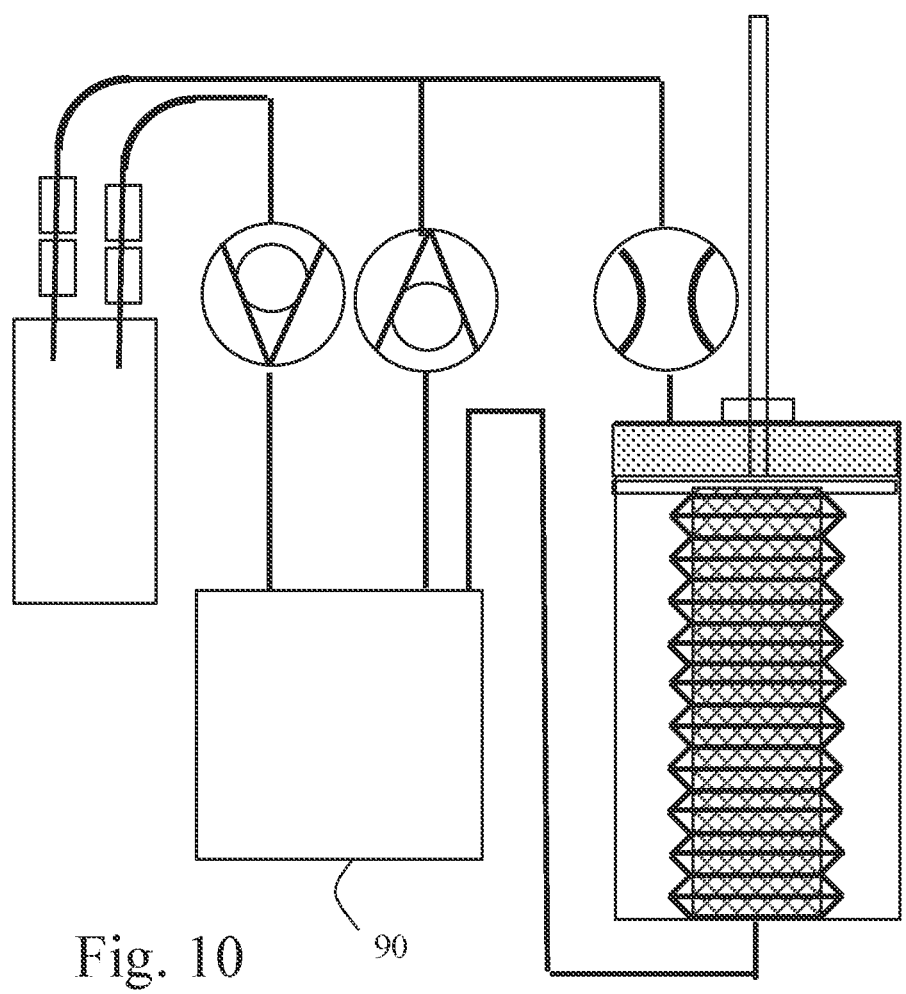
Fig. 10     90

APPARATUS FOR PERFORMING PERITONEAL ULTRAFILTRATION

FIELD OF INVENTION

The present invention relates to a manual apparatus for performing peritoneal ultrafiltration of a patient in need thereof, for example due to congestive heart failure.

BACKGROUND

Diuretic-resistant congestive heart failure is a problem of growing significance. It is related closely to the cardio-renal syndrome, which is characterized by chronic abnormalities in cardiac function, causing impaired renal function and progressive chronic kidney disease.

Congestive Heart Failure patients can benefit from fluid removal by ultrafiltration. These patients normally have functional kidneys, but suffer from fluid overload. The kidneys of these patients are generally healthy but are not fully functioning due to the failing heart with increased venous blood pressure and sometimes low arterial blood pressure. Because the kidneys are not fully functioning, fluids build up in the patient and the fluid overload contributes to stress on the already partly failing heart.

The proper control of sodium and water balance is of vital importance because up to 80% of hospitalizations from Congestive Heart Failure are due to acute over hydration and only 5% are due to low cardiac output.

The patent document US7135008B2 discloses a method and apparatus for the extracorporeal treatment of blood by utilizing a dual lumen catheter assembly peripherally inserted in the blood vessels for the continuous removal and return of blood for renal replacement treatment, in particularly, treatment of congestive heart failure and fluid overload by ultrafiltration. A catheter is inserted in a peripheral vein and maneuvered upward through the vascular system to access the reservoir of blood in the large or great veins for continuous blood withdrawal and treatment. Air-tight connectors are incorporated in the catheter assembly to overcome the untoward effects of negative pressure in blood withdrawal.

However, ultrafiltration via extracorporeal treatment of blood, results in risks associated with access to the vascular system. In addition, the ultrafiltration may be excessive resulting in hypotension.

A promising ultrafiltration method which do not use extracorporeal blood treatment is used in peritoneal dialysis, in which the endogenous peritoneal membrane is used for ultrafiltration. A peritoneal ultrafiltration fluid is instilled in the peritoneal cavity. The fluid comprises an osmotic agent, such as glucose or Icodextrin or others, causing ultrafiltration. Peritoneal ultrafiltration is more gentle to the patient and seldom results in hypotension. In addition, peritoneal ultrafiltration may be used daily outside the hospital without or with limited need for medically trained professionals.

With the present PD regiments, such as CAPD, glucose based fluids are replaced every two to four hours and has optimal ultrafiltration for only 2 to 3 hours or less. Each replacement may take up to one hour and increases the risk of infection. This reduces the freedom and quality of life for the patients.

In addition, the use of glucose may result in the absorption of glucose into the circulation, which may lead to hyperglycemia, hyperinsulinemia, and obesity. Icodextrin may cause other problems.

Addition of an osmotic agent to the peritoneal cavity may be detrimental to the peritoneal membrane if the concentration of the osmotic agent is excessive. Thus, the peritoneal membrane needs to be protected from local high concentration of osmotic agent, such as glucose, especially at the introduction site of the peritoneal cavity.

A peritoneal dialysis apparatus is disclosed in patent document WO2013109922A1. The document discloses a dialysis system comprising: a sorbent cartridge in fluid communication with at least one of a patient or a dialyzer, the sorbent cartridge including a housing having a zirconium phosphate layer followed by at least one of a urease layer, a zirconium oxide layer, or a carbon layer; a storage container in fluid communication with the sorbent cartridge; a pump in fluid communication sorbent cartridge and the storage container; and a control unit in operable communication with the pump, wherein the control unit is programmed to cause the pump to pump a dialysis fluid to flow (i) in a first direction through the sorbent cartridge, wherein the zirconium phosphate layer is contacted by the dialysis fluid before the at least one of the urease layer, zirconium oxide layer or carbon layer and (ii) in a second direction, reverse from the first direction, through the sorbent cartridge wherein the at least one of the urease layer, zirconium oxide layer or carbon layer is contacted by the dialysis fluid before the zirconium phosphate layer. The dialysis system, when used for peritoneal dialysis, removes all peritoneal fluid in the peritoneal cavity, and pass the fluid through an adsorption cartridge into a receptacle, in which glucose (and other substances) may be replenished, whereupon the peritoneal fluid is returned to the peritoneal cavity, see FIG. 19 of WO2013109922A1. Removal of all dialysis fluid takes time, which decreases the effective treatment time correspondingly.

Thus, there is a need for an apparatus for providing a peritoneal fluid to the peritoneal cavity, which is optimized with regard to peritoneal ultrafiltration of patients with heart failure.

The patients having need for peritoneal ultrafiltration may need an apparatus for performing the ultrafiltration method, which is transportable and may be carried by the patient, so that the patient is not tied to any stationary equipment. Furthermore, the apparatus should be simple to use.

SUMMARY OF THE INVENTION

Accordingly, an object of the present invention is to mitigate, alleviate or eliminate one or more of the above-identified deficiencies and disadvantages singly or in any combination.

In an aspect, there is provided an apparatus for performing ultrafiltration of a patient, for example a patient being overhydrated due to congestive heart failure, comprising: a patient line comprising a patient connector for connection to a peritoneal catheter connector for access to a peritoneal cavity of the patient; a dilution receptacle connected to the patient line for removal and return of peritoneal fluid to and from the peritoneal cavity; a glucose receptacle comprising glucose concentrate to be mixed with the contents of the dilution receptacle and subsequent introduction of the mixture into the peritoneal cavity; a metering device for metering an amount of glucose which is proportional to an amount of fluid removed from the patient at each time instance; whereby glucose is replenished intermittently for keeping a concentration of glucose substantially constant in the peritoneal cavity.

According to an embodiment, the dilution receptacle may be a syringe having a retractable piston and a syringe stem for operation of the piston, and wherein the apparatus further comprises: a UF receptacle; a first valve and a second valve; wherein the first valve is arranged for connection of the syringe with said patient tube in a first position, and for connection of the syringe with the second valve in a second position; the second valve may be arranged for connection of the first valve to the UF receptacle in a first position, and for connection of the first valve to the glucose receptacle in a second position.

According to another embodiment, the glucose receptacle and the UF receptacle may be arranged as syringes each comprising a syringe stem attached to a corresponding piston and a nut arranged moveable along the syringe stem for limiting the movements of the pistons inside each syringe.

According to a further embodiment, the dilution receptacle may be a first syringe having a piston and a syringe stem for operation of the piston, and wherein the apparatus further comprises a second syringe having a retractable piston and a syringe stem for operation of the piston, and wherein the glucose bag comprises an enclosure having a constant volume, and a partition wall dividing the enclosure into two compartments, a first of which comprising glucose concentrate and a second of which comprising peritoneal fluid, and wherein introduction of peritoneal fluid inside the second compartment displaces an equal volume of glucose concentrate out of the first compartment.

According to a still further embodiment, the dilution receptacle comprises a dilution syringe having a piston operated by a syringe stem and being connected to the patient line; and further comprising an ultrafiltration syringe having a piston and a syringe stem and being connected to the patient line via a one-way valve and further being connected to a combination bag via a second one-way valve, wherein said combination bag comprises a first compartment for ultrafiltration fluid and a second compartment comprising glucose concentrate, whereby inflow of ultrafiltration fluid in said first compartment results in an outflow of glucose concentrate, wherein the ratio between inflow and outflow is constant and larger than one, for example 5:1.

In another aspect, there is provided a method of performing ultrafiltration of a patient, for example a patient being overhydrated due to congestive heart failure, comprising: removal of an ultrafiltration volume from a peritoneal cavity of the patient; removal of a peritoneal fluid from a peritoneal cavity of the patient to a dilution receptacle; addition of glucose to the dilution receptacle, wherein an amount of glucose is added, which is proportional to said ultrafiltration volume removed from the patient at each time instance; returning of said mixture of peritoneal fluid and glucose in said dilution receptacel to the peritoneal cavity of the patient; and repeating said method steps.

In an embodiment, the method steps may be repeated with a time interval of between 10 minutes and 60 minutes, such as about 30 minutes. The proportionality constant may be determined empirically for each patient.

BRIEF DESCRIPTION OF THE DRAWINGS

Further objects, features and advantages of the invention will become apparent from the following detailed description of embodiments of the invention with reference to the drawings, in which:

FIG. 1 is a set of diagrams in which

FIG. 2 is a set of diagrams in which

FIG. 10 is a schematic diagram of the fourth embodiment according to FIG. 8 adapted to a patient having a double lumen catheter.

DETAILED DESCRIPTION OF EMBODIMENTS

Figure 1A:
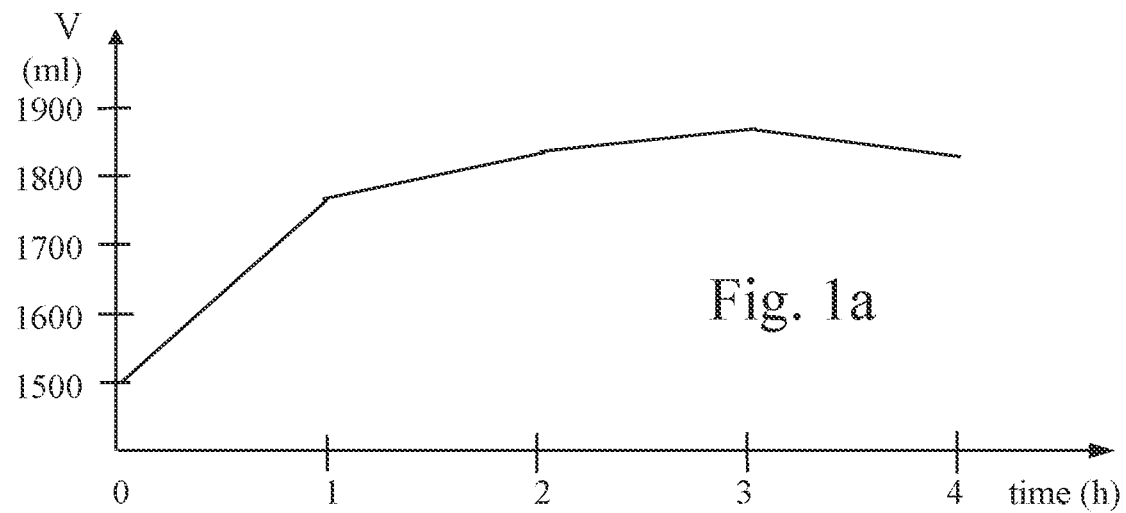
FIG. 1a shows intraperitoneal fluid volume.

Below, several embodiments of the invention will be described. These embodiments are described in illustrating purpose in order to enable a skilled person to carry out the invention and to disclose the best mode. However, such embodiments do not limit the scope of the invention. Moreover, certain combinations of features are shown and discussed. However, other combinations of the different features are possible within the scope of the invention.

An apparatus for performing a peritoneal ultrafiltration method may in principle be constructed similar to an apparatus for performing peritoneal dialysis. However, different methods of optimizations are due since these two apparatuses perform different medical treatments.

It is noted that an apparatus for performing peritoneal dialysis may simultaneously be arranged for performing peritoneal ultrafiltration. However, the task to remove unwanted products, such as urea and creatinine, is normally the focus. Thus, a peritoneal dialysis apparatus is normally arranged for removing such unwanted products, for example by adsorption, or by dialysis, while the glucose concentration is normally of less importance. See for example the patent document WO2013109922A1, mentioned above. Thus, the ultrafiltration may become less than optimal.

On the other hand, a peritoneal ultrafiltration apparatus is optimized for providing ultrafiltration without overloading the patient with glucose, while removal of unwanted products (such as urea) is of secondary importance. In addition, a gentle ultrafiltration is desired in order to avoid complications for overhydrated congestive heart failure patients.

The peritoneal dialysis/ultrafiltration method is preferred over hemodialysis, since the patient is free from hospitalization and can perform the peritoneal dialysis/ultrafiltration method at home or at any place. In addition, the peritoneal dialysis/ultrafiltration method can be performed more often, for example 10 to 16 hours daily during daytime or 8 to 12 hours during nighttime.

The present embodiments of the dialysis ultrafiltration apparatus and method according to the invention is constructed having the following precautions in mind:

1) Use of heavy mechanical devices such as pumps driven by electric batteries should be avoided or minimized. The patient should be able to carry the apparatus all the treatment time.

2) The treatment should be able to be performed with only human forces by the patient himself.

3) For optimizing ultrafiltration and minimizing body absorption of glucose, a low and substantially constant concentration of glucose should be used and a substantially constant volume of fluid should be maintained in the peritoneal cavity.

4) High intraperitoneal pressure should be avoided.

5) Exposure of the entrance area of the peritoneal cavity from high glucose concentration should be avoided.

The peritoneal dialysis method most frequently used today is CAPD. During this method, a high volume of peritoneal dialysis fluid is instilled in the peritoneal cavity, for example four times per day. The peritoneal dialysis fluid is maintained in the peritoneal cavity during for example 2 hours to 4 hours. Then, the peritoneal fluid is removed and discarded and fresh dialysis fluid is instilled, which normally takes about 30 minutes or more. The volume of peritoneal fluid instilled each time is normally between 1200 ml and 2400 ml or as much as the patient can take. If an ultrafiltration of 400 ml per exchange should be obtained, the volume removed will be 400 ml larger.

The use of high volumes results in a relatively high pressure in the peritoneal cavity. Such high pressure will counteract ultrafiltration. In order to reduce the intraperitoneal pressure, it may be advantageous to remove fluid more often than each second or fourth hour, in order to keep the intraperitoneal fluid volume below a specific volume, at which the intraperitoneal pressure increases more rapidly.

CAPD uses different glucose concentrations in dependence of the need of a patient. The glucose concentrations normally range from 1.5% to 4.25%. However, several reports have indicated that high glucose concentrations may result in compromised peritoneal function, at least during long time exposure. Thus, the present embodiments endavour the use of a maximum glucose concentration, which is lower than 4.25%. Below, a maximum concentration of 3.0% will be used as an example. Other maximum concentrations can be used, such as 4.0%, 3.9%, 3,8%, 3.7%, 3.6%, 3.5%, 3.4%, 3.3%, 3.2%, 3.1%, 3.0% 2.9%, 2.8%, 2.7%, 2.6%, 2.5%, 2.4%, 2.3%, 2.2%, 2.1%, 2.0% or even lower.

In CAPD, a high initial glucose concentration is used. Glucose may have a halftime of about 40 to 120 minutes, resulting in a 50% reduction of the glucose concentration during such halftime. Thus, at least about 75%, or more, of the glucose contents may be absorbed during a CAPD dwell, resulting in absorption of about 65 gram glucose per dwell for 4.25% for the highest concentration of glucose in 2 liter solution and up to 22 gram glucose for 1.5%. However, CAPD with 1.5% glucose results in an ultrafiltration, which may be too small.

Fluid inside the peritoneal cavity is absorbed via lymphatic reabsorption and other routes which may be about 1 to 4 ml/min. Thus, if the glucose concentration is reduced to below a specific concentration, ultrafiltration previously obtained is removed and no net ultrafiltration is obtained. Such specific glucose concentration when ultrafiltration is balanced by lymphatic reabsorption may be in the range of 0.3% to 0.7%.

If the intraperitoneal pressure is elevated, the lymphatic reabsorption increases. During filling of the peritoneal cavity of a patient with peritoneal fluid, the pressure in the peritoneal cavity is relatively constant, such as 12 mmHg during filling up to a specific volume of for example about 1800 ml. If further fluid is installed, the pressure rises, since the compliance of the peritoneal cavity decreases. Thus, an installed fluid volume of 2000 ml may correspond to a pressure of about 14 mmHg and a fluid volume of 2200 ml may correspond to a pressure of about 18 mmHg.

Figure 1B:
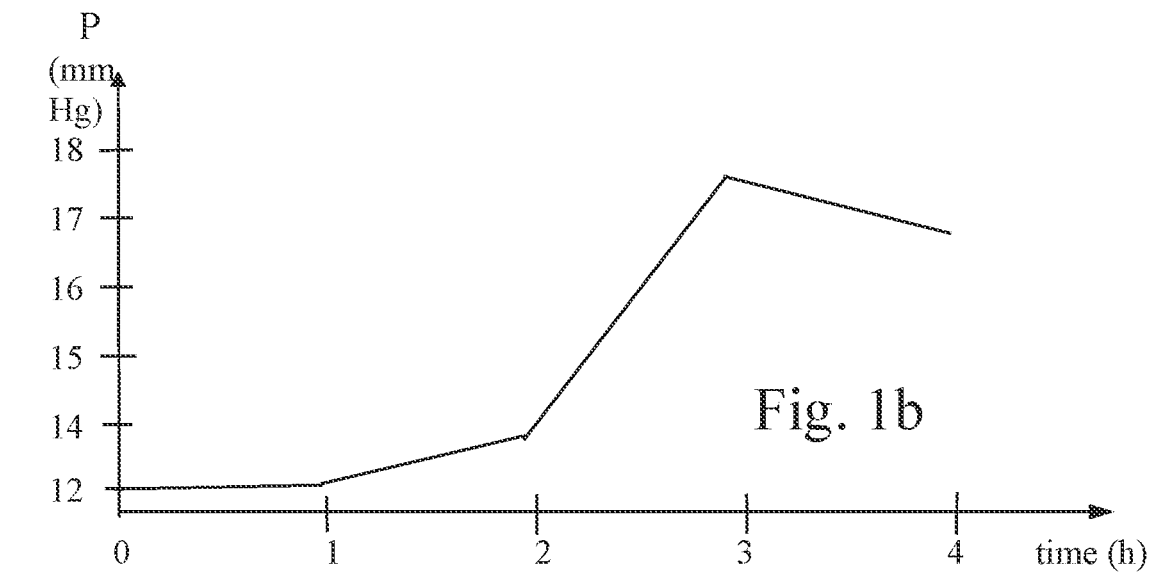
FIG. 1b shows intraperitoneal pressure and FIG. 1c shows intraperitoneal glucose concentration for a CAPD treatment.
Figure 1C:
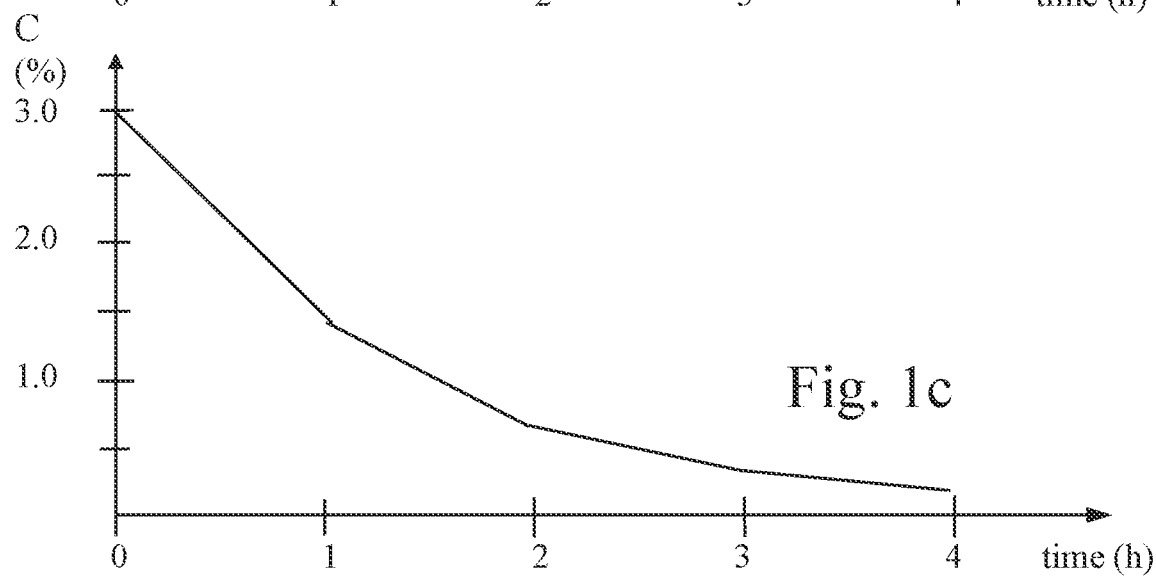

FIG. 1 is a set of diagrams, wherein FIG. 1a shows the intraperitoneal volume of fluid during a CAPD exchange of a specific patient. Initially, 1500 ml of fluid is installed. During the installation procedure, the intraperitoneal pressure was almost constant and about 12 mmHg, as shown in FIG. 1b. The initial glucose concentration was 3.0% as shown in FIG. 1c.

After about 60 minutes, the glucose concentration had decreased to 1.5%, which indicates a half-time of 60 minutes for the glucose. The volume had increased by 260 ml during 60 minutes, and the pressure was about 12 mmHg.

After the next 60 minutes, the glucose concentration had decreased to 0.75%. The pressure had increased to 14 mmHg, which resulted in increased reabsorption. Thus, the volume had increased by only 110 ml, compared to the expected 130 ml.

After the next 60 minutes, the glucose concentration had decreased to 0.38% and the volume had increased by 25 ml to a maximum after about 2.9 hours. The pressure was about 18 mmHg.

During the next 60 minutes, the glucose concentration was 0.19% and there was a net absorption of fluid, resulting in a decrease of fluid of 8 ml. The pressure had decreased to 17 mmHg.

During 4 hours of dwell, a total of 387 ml had been ultrafiltrated and 42 g of glucose had been adsorbed by the patient.

The same patient was exposed to treatment according to the present invention, as shown in the set of diagrams of FIG. 2.

A fluid volume of 1500 ml was installed with an initial glucose concentration of 1.0%. The intraperitoneal pressure was 12 mmHg.

After 30 minutes, the volume had increased by 50 ml. The glucose concentration had decreased to about 0.71% and the pressure was still 12 mmHg.

The inventors have found that if a substantially constant glucose concentration is arranged in the peritoneal cavity, a relatively low maximum concentration of glucose can be used. In addition, a high initial ultrafiltration is not beneficial but a small but persistent ultrafiltration will do better. Thus, a low glucose concentration and a low intraperitoneal pressure are desired.

On the other hand, the peritoneal cavity should be filled with fluid so that the complete intraperitoneal membrane is used for ultrafiltration. This will enable a reduction of the glucose concentration for obtaining a specific goal of ultrafiltration volume.

For a specific patient to be discussed below, in which 1500 ml peritoneal fluid of 1.0% glucose concentration had been instilled, it has been determined that the glucose removal rate at 1.0% glucose concentration was about 0.1 mg/min and the net ultrafiltration was about 3 ml/min. During the course of time, the glucose concentration decreased and was about 0.71% after 30 minutes and the net ultrafiltration was 1.5 ml/min. After another 30 minutes, the glucose concentration was 0.5% and the net ultrafiltration was zero, which means that the osmotic ultrafiltration due to glucose was balanced by lymphatic reabsorption of water.

In order to maintain the concentration above 0.71%, it was required to replenish 4.35 gram of glucose per 30 minutes in order to restore the concentration to 1.0%. In order to maintain the lymphatic reabsorption sufficiently below the osmotic ultrafiltration, a removal of about 50 ml fluid per 30 minutes was desired in order to keep the intraperitoneal pressure sufficiently low and maintain the intraperitoneal volume substantially constant.

Figure 2A:
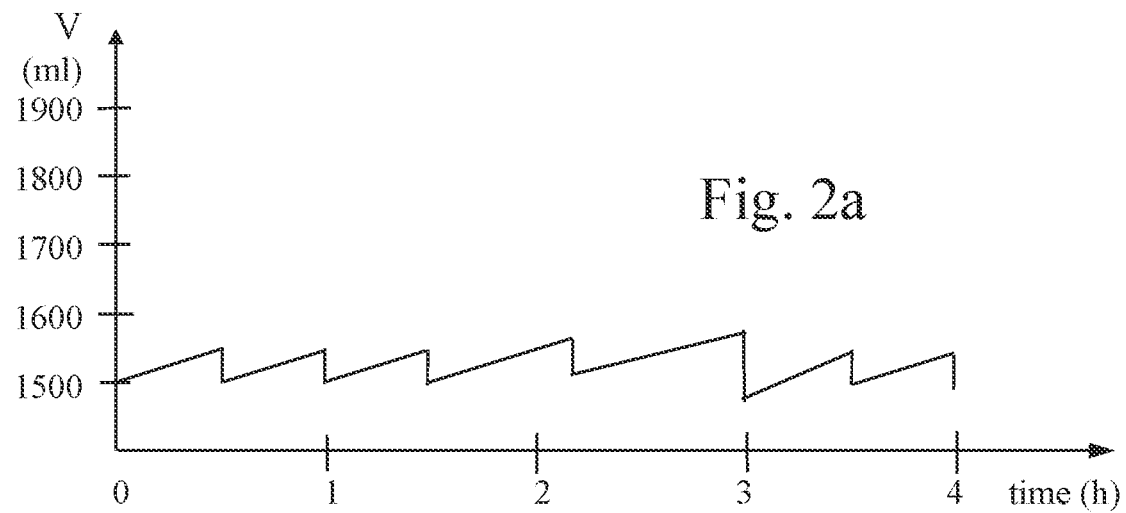
FIG. 2a shows intraperitoneal fluid volume.
Figure 2B:
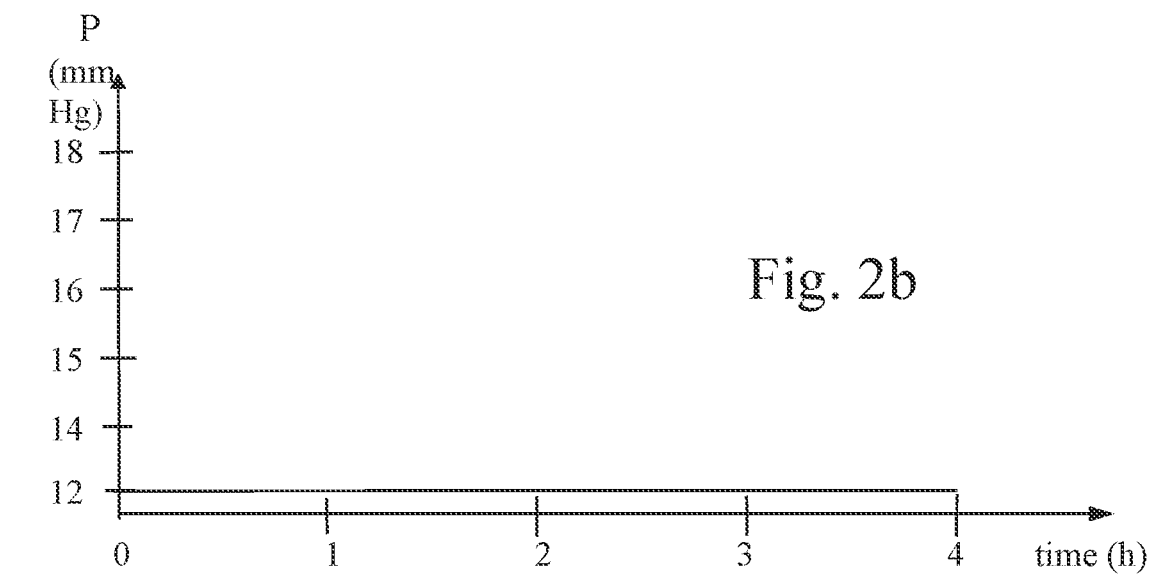
FIG. 2b shows intraperitoneal pressure and FIG. 2c shows intraperitoneal glucose concentration for an ambodiment of the present invention.
Figure 2C:
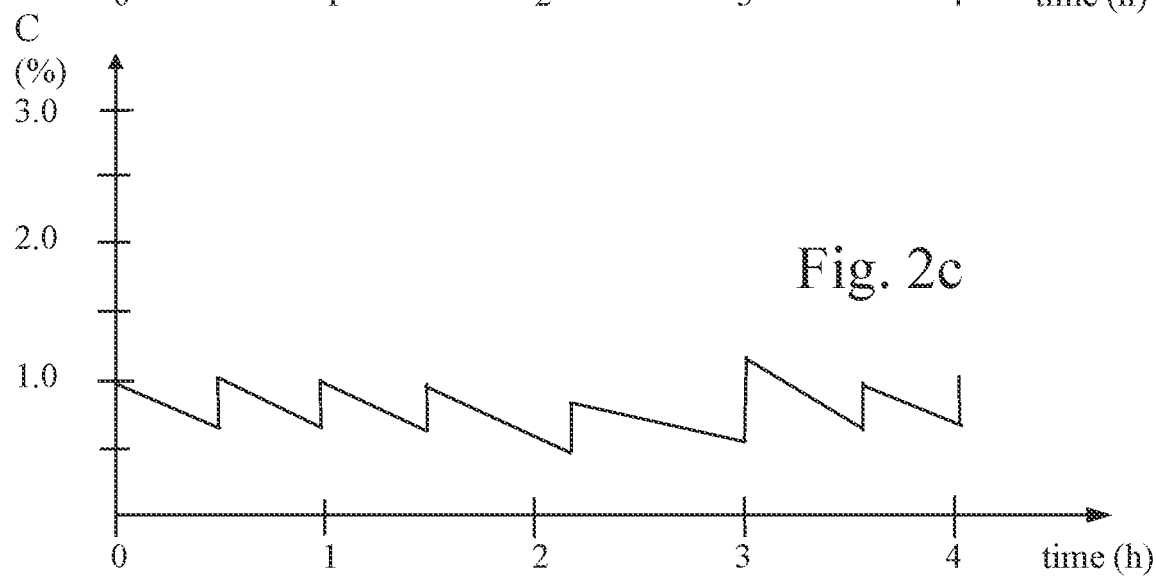

As shown in FIG. 2a, the fluid volume started at 1500 ml and increased to 1550 ml, whereupon 50 ml was removed. Three consecutive removals are shown at 30 minutes intervals. As shown in FIG. 2c, the glucose concentration started at 1.0% and decreased to 0.7% during 30 minutes and was then restored to 1.0% by addition of 4.35 g of glucose. As shown in FIG. 2b, the intraperitoneal pressure was substantially constant at 12 mmHg.

After 1.5 hours, there is shown that the time interval of removal increased to 40 minutes and 50 ml was removed at time 2 hours and 10 minutes. Since the fluid volume had increased more than 50 ml, the net result was that 1520 ml remained in the peritoneal cavity, as shown in FIG. 2a. The glucose concentration after replenishment with 4.35 g of glucose was about 0.95%. Thus, the ultrafiltration became slower, as shown by the inclination of the volume line.

At time instance of 3 hours, 100 ml of fluid was removed and 8.70 g of glucose was added. The result was that the fluid volume decreased to 1470 ml and the glucose concentration became 1.05%. At time instance 3.5 hours, 50 ml was removed and 4.35 g of glucose was added. Finally at time instance 4 hours, 50 ml was removed and 4.35 g of glucose was added.

The net result is that 400 ml of fluid was removed and 34.8 g of glucose was used during four hours. The treatment can be continued for longer times or shorter times.

An important advantage of the invention is that the glucose concentration was below 1.0% except for a short time period. Thus, the peritoneal membrane is saved.

The inventor has found that if the amount of glucose added is proportional to the volume of fluid removed, a substantially constant volume and glucose concentration can be obtained. In the example given above with reference to FIG. 2a to FIG. 2c, the constant is:

$$K = 50 \text{ ml}/4.35 \text{ g}$$

If the additions/removals takes place often, the variations in concentration and fluid volume can be minimized.

The constant is determined empirically for each patient. For example, if it is determined that the volume of fluid after an treatment has increased, for example from an installed volume of 1500 ml to a finally removed volume of 1600 ml after four hours, this is an indication that the constant is too high. Thus, the constant can be reduced during the next treatment—and vice versa.

The apparatus according to embodiments should be constructed so that it can be carried by the patient during a daily treatment time of 10 hours. Thus, it is essential that the weight of the apparatus including fluids will be as small as possible. If 3% glucose concentration fluid is used, which is considered to be safe for introduction into the peritoneal cavity, more than 3 liters of fluid would be required per 10 hours treatment. Thus, a glucose replenishment solution having a higher concentration of glucose is desired, such as 10% (900 ml) or 30% (300 ml).

Fluid having 30% glucose concentration should not be infused directly into the peritoneal cavity, since such infusion may result in tissue damages and compromised function, at least during long term exposure.

In order to dilute the high concentration glucose solution, some fluid is removed from the peritoneal cavity in order to dilute the glucose concentrate. If 4.35 g of glucose should be entered, 176 ml of peritoneal fluid (having a concentration of about 0.7%) would be required for diluting 14.5 ml of 30% glucose concentrate to a final concentration of about 3% (190.5 ml). Below, this will be rounded to 15 ml and 4.5 g glucose and 175 ml of dilution fluid. Such replenishment is made with 30 minutes intervals.

The above mentioned data was given for a specific patient in order to elucidate the embodiments below. However, such data may vary over time for the specific patient. In addition, each patient has his own characteristic data. Thus, glucose infusion rate and UF fluid removal rate may be adjusted to the specific person and may be adjusted over time. There are several theoretic works describing the transport kinetics, for example by a three-pore-model.

Figure 3:
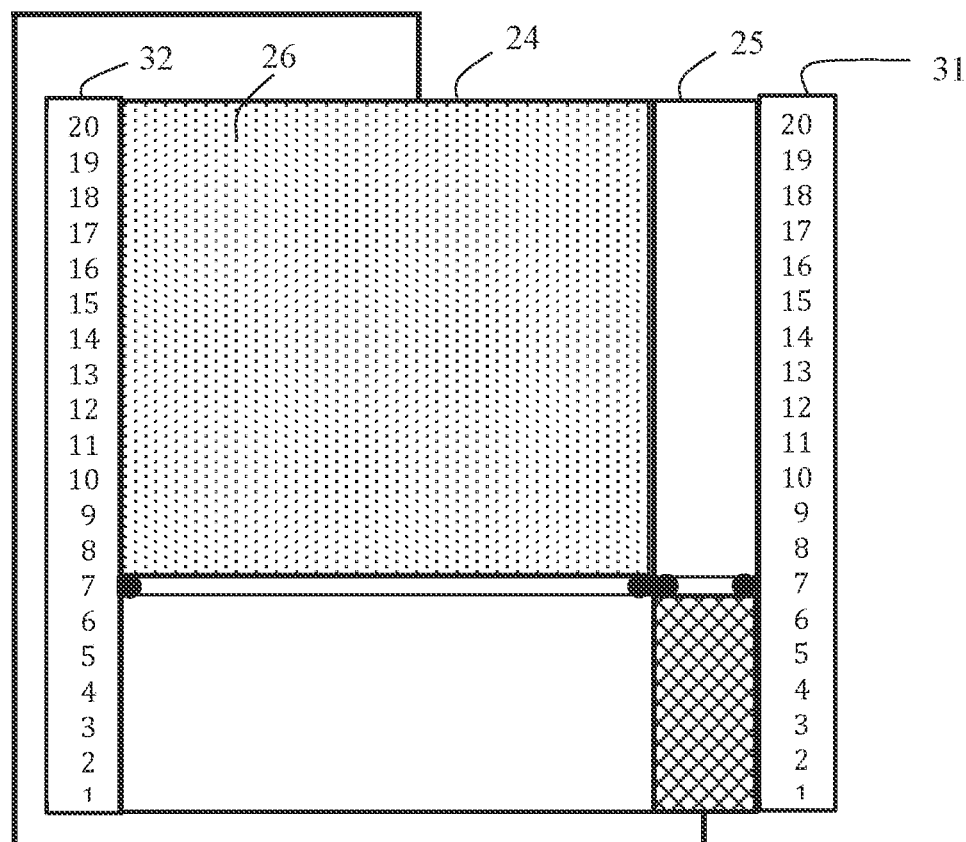
FIG. 3 is a schematic diagram of a first embodiment of an apparatus for providing an ultrafiltration fluid to a patient.
Figure 3:
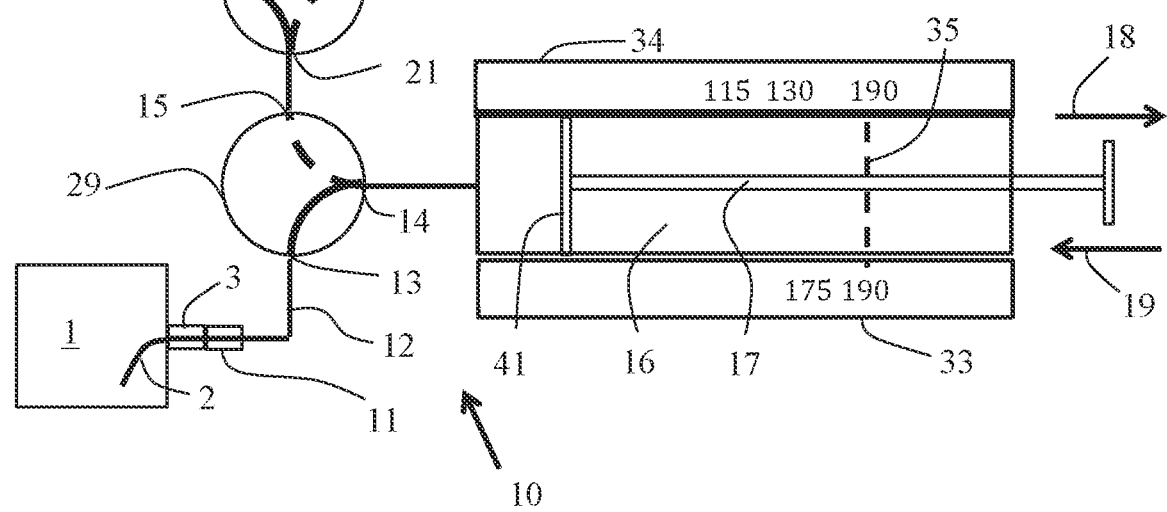

A first embodiment of an apparatus for performing the above glucose infusion and fluid removal is disclosed in FIG. 3.

A peritoneal cavity of a patient is shown schematically at 1. A peritoneal catheter 2 is arranged for communicating fluid into and out of the peritoneal cavity. The peritoneal catheter 2 ends in a connector 3, which is arranged to be connected to a patient connector 11 of the ultrafiltration apparatus 10, preferably by an aseptic method normally used in for example CAPD or APD.

The apparatus 10 further comprises a patient tube 12, at one end connected to said connector 11 and at the other end connected to a first inlet/outlet 13 of a first two-way valve 29. A second inlet/outlet 14 of the first valve 29 is connected to a syringe 16 having a syringe stem 17 for controlling the volume inside the syringe by moving a piston 41 inside the syringe. In the position of the first valve 29 shown by solid lines, the syringe 16 may withdraw peritoneal fluid from the peritoneal cavity of the patient by exerting a pulling action on syringe stem 17 as shown by arrow 18. The syringe 16 may have a volume of about 250 ml or slightly larger.

A second two-way valve 20 is connected to a third inlet/outlet 15 of the first valve 29 via a first inlet/outlet 21 of the second valve 20. A second inlet/outlet 22 of the second valve 20 is connected to a large syringe 24 having a volume of about 1500 ml, which corresponds to a desired total ultrafiltration volume of 1200 ml over 10 hours plus the volume of infused glucose solution, 300 ml. A third inlet/outlet 23 of the second valve 20 is connected to a third syringe 25 having a volume of 300 ml and comprising glucose concentrate at a concentration of 30%, thus initially comprising 90 gram of glucose. The pistons of the second and third syringes may be used for indicating the filling level of the syringe by means of gradings 31, 32, which are graded in 20 half-hours.

A replenishment cycle is as follows: Initially, the first valve 29 is arranged in the position shown by solid lines in FIG. 3 where after the piston rod 17 is pulled as shown by arrow 18 in order to fill the first syringe 16 with peritoneal fluid taken from the peritoneal cavity. About 250 ml is removed, resulting in that the syringe is full. Then, the first valve 29 is switched to an alternate position shown by broken lines in FIG. 3 and the piston rod 17 is pushed in the other direction as shown by arrow 19 in order to pass fluid from the first syringe 16 into an upper compartment 26 of the ultrafiltration syringe 24. The piston rod 17 is operated until 75 ml of fluid has been entered into compartment 26 of syringe 24 and 175 ml of fluid is left in the syringe 16. The syringe may be provided with a grading or scale, which indicates the positions. There may alternatively be a shoulder which indicates when 75 ml has been removed from the syringe.

Then, the second valve 20 is moved to an alternate position shown by broken lines in FIG. 3, whereupon the piston rod 17 is pulled according to arrow 18 until 15 ml of glucose concentrate has entered the first syringe 16, resulting in 190 ml of fluid in the first syringe 16. The glucose concentrate will mix with the contents of the first syringe, which totally is about 190 ml of fluid, whereby the glucose is diluted to a concentration below 3%. There may be gradings or alternatively a shoulder which indicates when 15 ml has been entered into the syringe.

Finally, the two valves are returned to the positions shown by solid lines in FIG. 3 and the piston rod 17 of the first syringe 16 is pushed for moving all the remaining fluid (190 ml) via valve 29 into the peritoneal cavity. The end result is that 4.5 gram of glucose or 15 ml of glucose solution has entered the peritoneal cavity after being diluted to below 3%. In addition, 75 ml of ultrafiltration fluid has been removed from the peritoneal cavity, resulting in a net UF of 60 ml. Other volumes may be used, such as 50 ml as mentioned above in connection with FIG. 2.

As shown, the pistons of the second syringe 24 and the third syringe 25 will move substantially in unison if correct volumes are removed during use, because the diameters of the two syringes are correspondingly related. The gradings 31 and 32 at the syringes 24 and 25 may be used for control. Thus the constant K=60 ml/4.5 g The syringes 24 and 25 may be replaced by flexible bags, a glucose bag 25 initially comprising 300 ml of glucose concentrate at 30% and a UF bag 24 initially being empty and having a final volume of 1500 ml or larger. In this case it will not be possible to determine the volumes of the bags during operation. However, the correct operation is assured by the gradings 33, 34 of the syringe 16.

The total volume of the first syringe may be larger than 250 ml, since that only results in that the glucose concentration in the fluid entered into the peritoneal cavity will lower than 3.0%. Thus, the syringe may have a volume of 250 ml, 260 ml, 270 ml, 280 ml, 290 ml, 300 ml or larger.

Alternatively, the removal of ultrafiltration fluid and the replenishment of glucose can be made in two separate steps, whereby a smaller syringe can be used, having a volume of 190 ml or slightly larger as shown by broken line 35 in FIG. 3. In an ultrafiltration step, the first piston is pulled in order to fill the syringe with 190 ml of peritoneal fluid while the valves are arranged as shown by solid lines in FIG. 3. Then, the first valve 29 is arranged as shown by broken lines in FIG. 3 and the syringe is pushed according to arrow 19 until 75 ml of fluid has been moved to the upper compartment 26 of the second syringe 24 and the first syringe comprises 115 ml. Now, the second valve is arranged as shown by broken lines in FIG. 3 and 15 ml of glucose solution is entered into the syringe to a total volume of 130 ml by pulling the first syringe stem 17 as shown by arrow 18. Finally, the valves are arranged in the positions shown in solid lines in FIG. 3, and the syringe is pulled until the end position to enter another 60 ml of fluid into the syringe from the peritoneal cavity to a total amount of 190 ml, which will mix and dilute the glucose in the syringe to 3%. Finally, all solution inside the syringe is filled back to the peritoneal cavity by pushing the syringe stem 17 to the end position to the left in FIG. 3. It is desired to perform the UF step before the replenishment step.

The end result is that 4.5 gram of glucose or 15 ml of glucose solution has entered the peritoneal cavity after being diluted to below 3%. In addition 75 ml of ultrafiltration fluid has been removed from the peritoneal cavity, resulting in a net UF of 60 ml.

The process is repeated each 30 minutes. Alternatively, the process may be performed more often, for example with intervals of 10 minutes, 15 minutes or 20 minutes, or more seldom, for example with intervals of 40 minutes or 45 minutes or 60 minutes.

Figure 4:
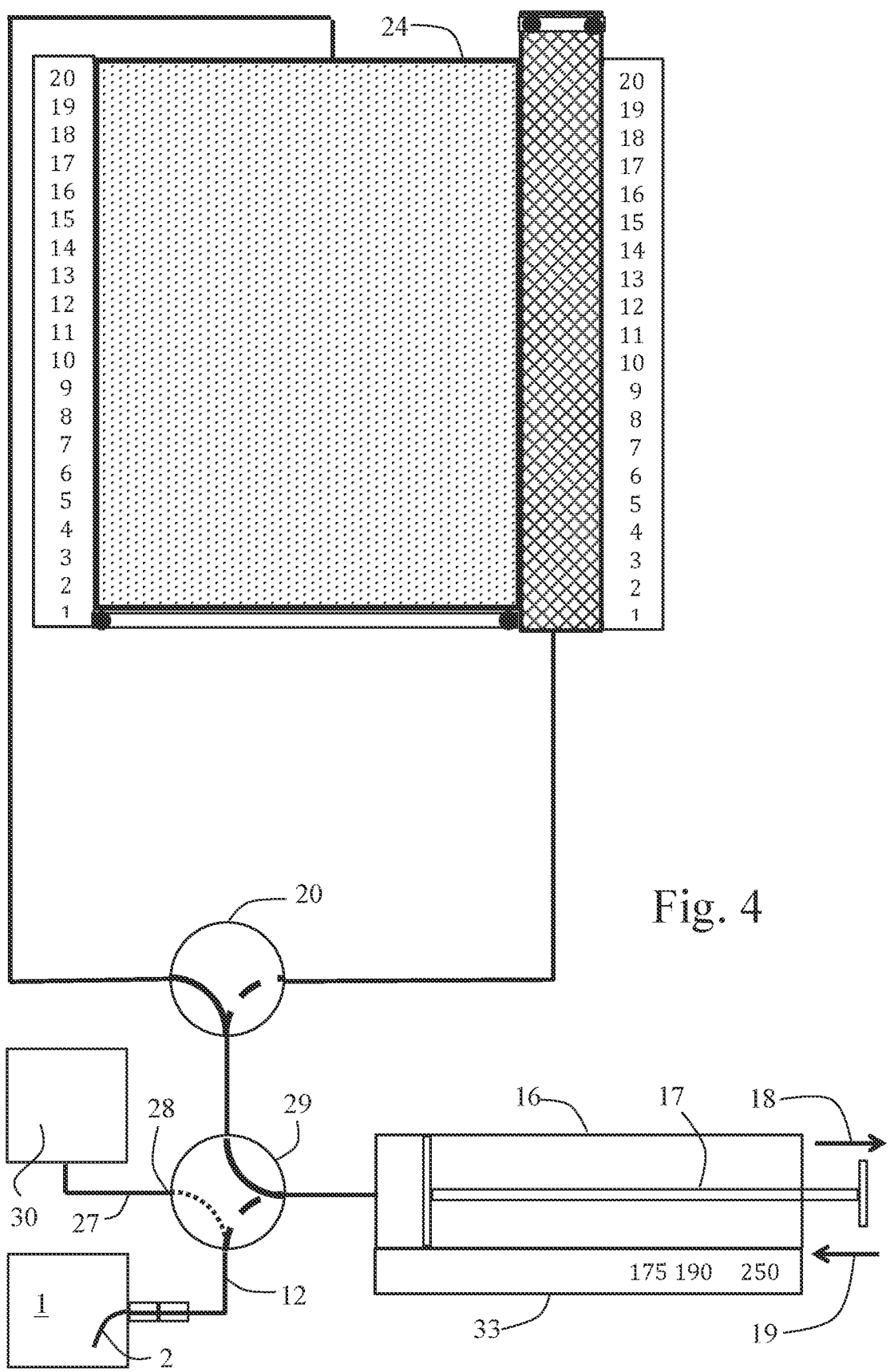
FIG. 4 is a schematic diagram of the first embodiment according to FIG. 3, including a fill bag feature.

The apparatus may also be used during the first fill as shown in FIG. 4, for example in the morning. In this situation, the second syringe 24 is initially filled with 1500 ml of fresh peritoneal fluid having a composition which is suitable for ultrafiltration, as discussed below. The peritoneal fluid in the second syringe lacks glucose. In addition, 345 ml of glucose solution is provided in the glucose syringe. The syringes 24 and 25 may be replaced by flexible bags, as indicated above.

First, the first syringe 16 is operated to be filled with fresh peritoneal fluid (250 ml) from the second syringe 24 with the valves arranges as shown in FIG. 4. Then, the first valve 29 is moved to the position shown in broken lines in FIG. 4 and the fluid is delivered to the peritoneal cavity by pushing the syringe rod 17 as shown by arrow 19. This process is repeated two times, whereby the peritoneal cavity comprises 500 ml peritoneal fluid without glucose. Next, the first syringe is filled with only 235 ml of fluid from UF syringe 24, whereupon the second valve 20 is arranged in the position shown in broken lines in FIG. 2 and 15 ml of glucose concentrate is entered into the first syringe 16. Finally, the first valve 29 is arranged in the position shown in broken lines in FIG. 4 and the contents of the syringe (250 ml) is filled into the peritoneal cavity to deliver 4.5 gram of glucose to the peritoneal cavity. This is repeated three times. Now, there is 1500 ml of fluid in the peritoneal cavity comprising 13.5 gram of glucose, which results in an initial glucose concentration of 0.9%. By this process, the peritoneal fluid initially entered into the peritoneal cavity during the first two operation steps is void of glucose and the glucose concentration is increased stepwise during the next three operation steps until 0.9% concentration. Such a gentle introduction may be advantageous for the peritoneal membrane.

The replenishment may be performed each 30 minutes. Infusion of 4.5 gram of glucose per 30 minutes will compensate for the glucose absorption and possibly increase the internal peritoneal glucose concentration until a balance is achieved, which may be larger or smaller than 0.9%, depending on the patients characteristics for glucose absorption and lymphatic reabsorption etc.

If a start concentration of glucose other than 0.9% is desired, for example 1.0%, the glucose in the three last steps is increased correspondingly (18 ml glucose solution per step).

Removal of ultrafiltration fluid, for example 60 ml each 30 minutes will ensure that the peritoneal cavity pressure does not increase.

By replenishment of glucose in an amount which is proportional to the ultrafiltration fluid, a substantially constant volume and a substantially constant glucose concentration can be obtained even if the replenishment/ultrafilteration is made with non-equal intervals.

Finally, after completion of the treatment after for example 10 hours, the peritoneal fluid inside the peritoneal cavity is drained into a drain bag. As shown in FIG. 4, a drain line 27 is connected to a fourth inlet/outlet 28 of the first valve 29. The drain line 27 ends in a drain bag 30 having a volume, which is larger than the expected drain volume (1500 ml), for example 2000 ml. By arranging the first valve 29 in the position shown by dotted lines and arranging the drain bag 30 at the floor, the peritoneal fluid will drain by gravity forces to the drain bag 30. Finally, the complete apparatus is weighted, and the increase of weight is noted as the ultrafiltration obtained.

The fill step may alternatively be performed by including the initial fresh peritoneal fluid (1500 ml) in the fill/drain bag 30, including glucose in a desired concentration. The initial fill is done by arranging the first valve 29 in the position shown by dotted line and arranging the fill/drain bag 30 at an elevated position, whereby the fluid inside the fill/drain bag 30 is filled into the patient peritoneal cavity via gravity forces.

In another alternative embodiment, the initial fresh peritoneal fluid in the fill/drain bag 30 does not include any glucose. After filling the peritoneal cavity, several (three) replenishment cycles are performed in order to increase the glucose concentration in a gentle manner. In this case, the UF syringe 24 should have a volume of 1500 ml plus 225 ml and the glucose syringe should have a volume of 345 ml. It is mentioned, that the two syringes may be arranged with a larger volume and contents than indicated above, for allowing for operation during more than 10 hours, or for having a safety margin.

There are several parameters, which may be adjusted. Since the apparatus is arranged to maintain the instilled fluid volume and the glucose concentration constant, the operation may be assessed by measuring these values. If the volume finally drained into drain bag is smaller than the initially instilled volume of 1500 ml, the ultrafiltration is too low. Thus, the replenishment of glucose is increased the next day and vice versa.

Alternatively, the fill/drain bag may comprise an excess of fluid, for example 2000 ml or 2500 ml, and is arranged at an elevated position, which is about 15 cm above the peritoneal entrance position, while the patient is sitting or standing. Now, the fluid flows into the peritoneal cavity until a balance is obtained, resulting in that the internal peritoneal pressure is about 15 cm water pillar (12 mmHg). Since the apparatus maintain the peritoneal fluid volume substantially constant, the intraperitoneal pressure will be maintained at such pressure.

Figure 5:
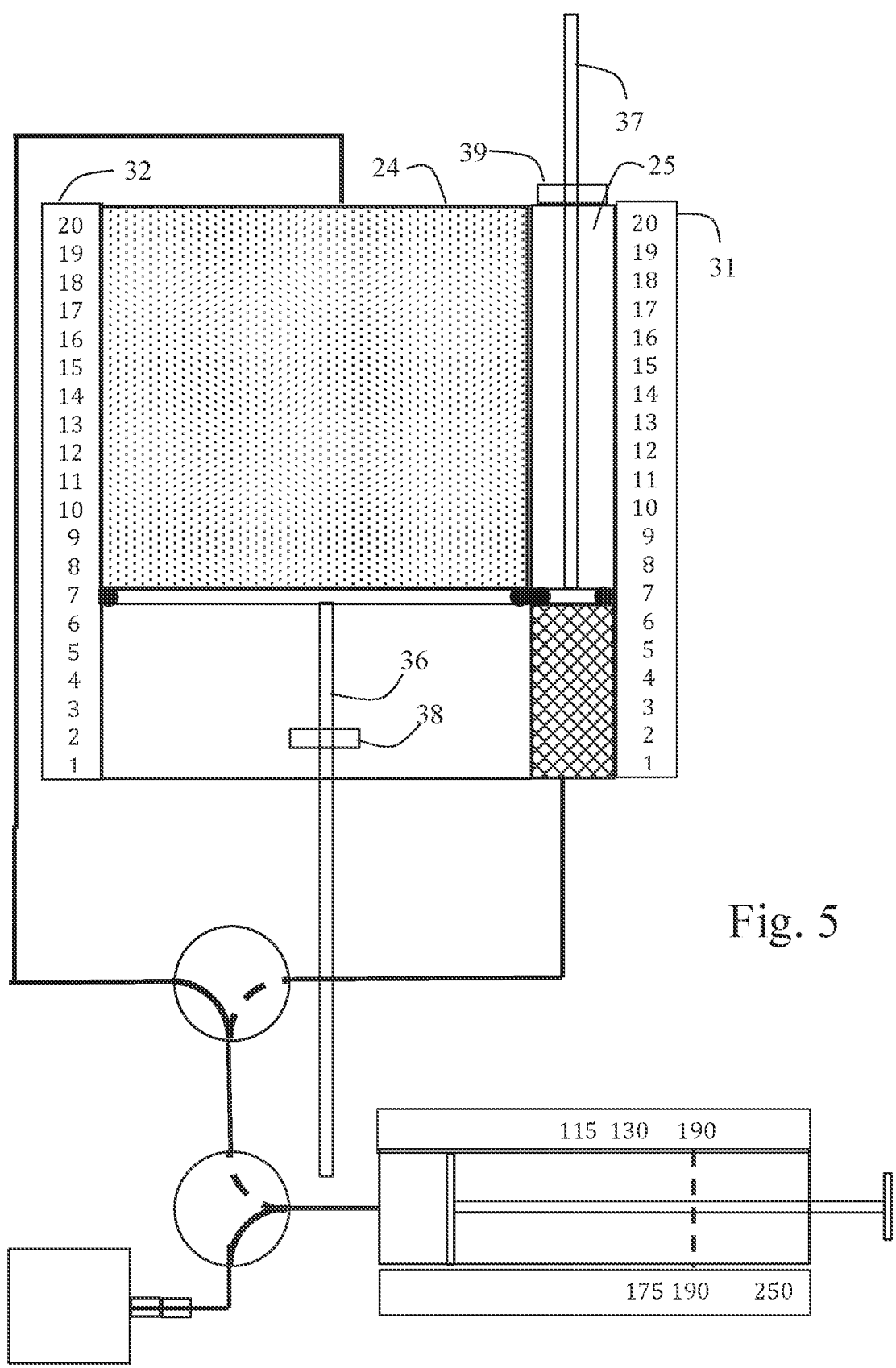
FIG. 5 is a schematic diagram of the first embodiment according to FIG. 3, including a further feature.

It may be difficult to measure the volumes of the ultrafiltration (75 ml) and the glucose solution (15 ml) at the gradings 33, 34 of the syringe and at the gradings 31 and 32 of the syringes 24 and 25. In an alternative design shown in FIG. 5, the syringes 24 and 25 are provided with syringe stems 36 and 37, which move together with the pistons of the syringes. Each syringe stem is provided with screw windings (not shown). A nut 38, 39 is arranged to cooperate with each stem 36, 37 screw winding. By rotation of the nut 38, 39 or by rotation of the stem 36, 37, the height position of the nut may be adjusted along the syringe stem. As shown in FIG. 5, the nut 38 of the ultrafiltration syringe 24 may be rotated to take a position slightly above the bottom of the syringe. Thus, inflow of fluid into the syringe 24 is allowed until the nut 38 has moved down into contact with the bottom of the syringe, which prevents further inflow of fluid into the syringe 24. The same is true for the glucose syringe but in the opposite direction. An adjustment of the nut 39 upwards one step will allow removal of glucose from the glucose syringe.

The adjustment may be arranged so that one revolution of the nut corresponds to 15 ml of removed glucose solution and 75 ml of entered ultrafiltration fluid. If the syringes have a height of 10 cm, each revolution corresponds to 0.5 cm.

It is also possible to do replenishments at any time interval. If an interval of 15 minutes is used, the nut is rotated half a revolution corresponding to 7.5 ml of glucose solution and 37.5 ml of ultrafiltration.

The nuts may be adjusted separately or may be connected for simultaneous rotation.

Figure 6:
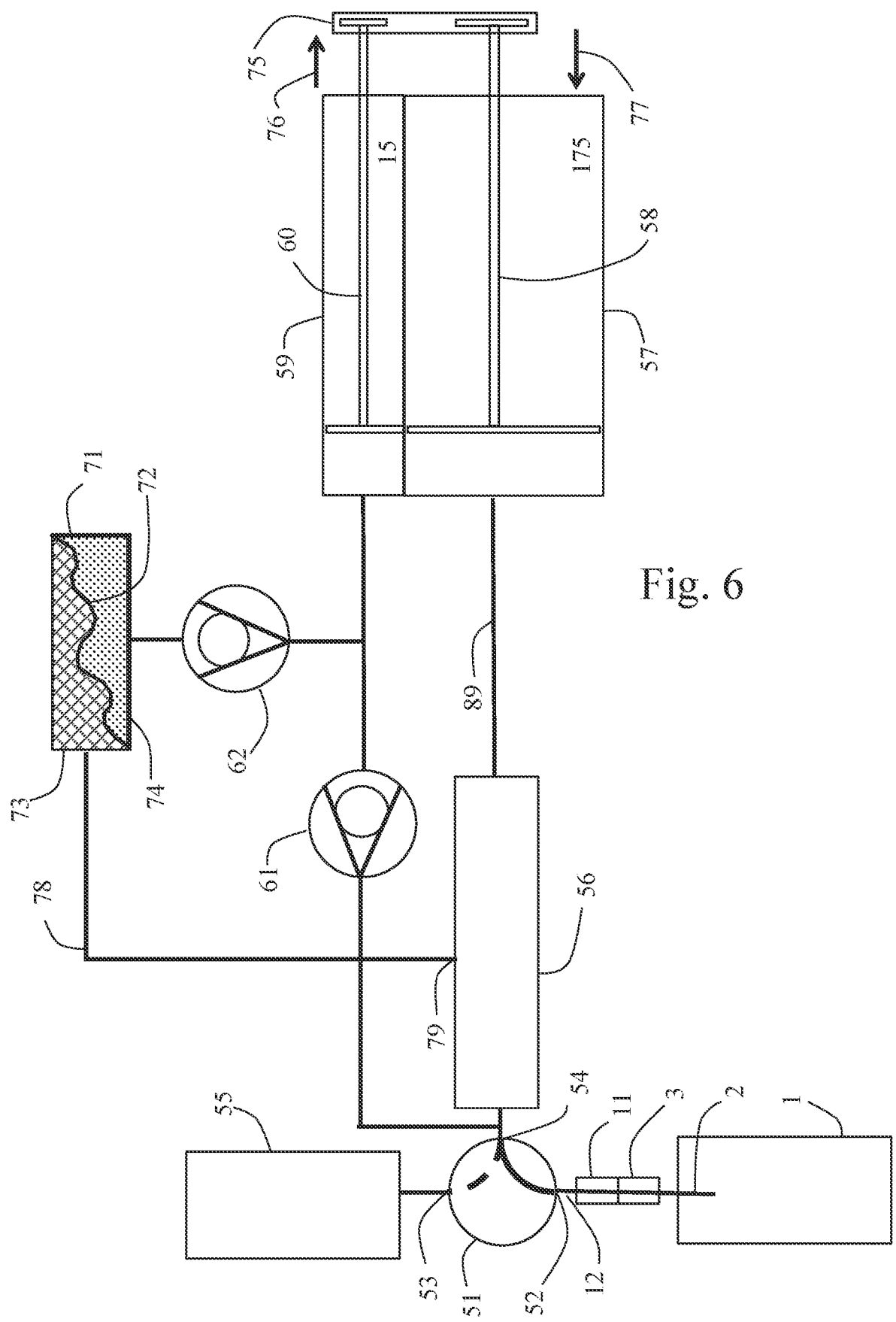
FIG. 6 is a schematic diagram of a second embodiment of an apparatus for providing an ultrafiltration fluid to a patient, comprising a dilution syringe and a glucose syringe.

In another embodiment, shown in FIG. 6, the apparatus comprises a patient peritoneal cavity 1, a catheter 2 and a connector 3. A patient connector 11 is connected to a patient line 12, the other end of which is connected to a first inlet/outlet 52 of a valve 51. A second inlet/outlet 53 of the valve 51 is connected to an ultrafiltration UF bag 55, which is flexible.

A third inlet/outlet 54 of the valve 51 is connected to a mixing chamber 56 and further to a first syringe 57 having a syringe stem 58. The third inlet is also connected via a first one-way valve 61 to a second syringe 59 having a second syringe stem 60. The second syringe 59 is also, via a second one-way valve 62, connected to a glucose bag comprising glucose solution at a desired concentration, for example 30%.

The glucose bag has non-flexible external walls 71, so that the interior volume is constant. The bag is divided in two compartments by a flexible partition wall 72. A first compartment comprises said glucose solution 73 and a second compartment 74 comprises peritoneal fluid.

The operation is as follows:

The syringe stems 58 and 60 are operated in unison by being interconnected by a syringe rod 75. In a first step, the syringes are filled with peritoneal fluid from the peritoneal cavity 1 by pulling the syringe rod 75 according to arrow 76. The first syringe 57 is filled with 175 ml of fluid and the second syringe 59 is filled with 15 ml of fluid. The sizes or diameters of the syringes are correspondingly dimensioned.

In a second step, the syringe rod 75 is pushed in the direction of arrow 77. Fluid in the second syringe 59 cannot pass back the same way as it came, because the one-way valve 61 blocks that path. Instead, the contents of the second syringe 59, via the second one-way valve 62, is entered into the second compartment 74 of the glucose bag 73. Because the glucose bag 73 is non-flexible, the entered volume displaces an equal volume of glucose solution out via a line 78, which ends in an inlet/outlet 79 in the middle side of the mixing chamber 56. Simultaneously, the first syringe 57 passes peritoneal fluid through the mixing chamber and the fluid from the first syringe 57 is mixed with the fluid displaced from the glucose bag compartment 73 via the second syringe 59. The mixture is the same as the ratio between the two syringes, 175 ml and 15 ml, which results in a solution having approximately 3% glucose concentration, which is entered into the peritoneal cavity. In addition, 15 ml of peritoneal fluid has been maintained in the compartment 74 of the glucose bag.

Such glucose replenishments takes place at regular intervals, for example each 30 minutes.

It is noted, that the mixing chamber 56 may be large or small, and even may be only a connection of the line 78 to the line 89 connecting the syringe 57 with the first valve 51.

As mentioned above, the volume of peritoneal fluid inside the peritoneal cavity will increase over time. When it is desired to remove some ultrafiltration fluid, the process is the same as above, with regard to the pulling of the syringe rod 75. However, before pushing the syringe rod 75, the first valve 51 is switched to the position shown in broken lines, which means that the fluid in syringe 57 and the glucose solution displaced by the second syringe 59 now instead is directed to the UF bag 55. Now, 190 ml of peritoneal fluid has been removed to the UF bag. If an ultrafiltration of 2 ml/min is desired, the UF process is repeated each 95 minutes.

In this process, glucose concentrate is passed to the UF bag 55, which may be regarded as a waist of glucose concentrate. However, glucose concentrate is inexpensive.

In an alternative method, the UF removal step is performed by making the syringe stem 58 of the first syringe 57 free from the syringe rod 75 and operating the first syringe 57 separately from the second syringe 59, which is maintained non-operated. Thus, 175 ml of ultrafiltration fluid is entered into the UF bag 55 without any extra glucose.

The replenishment step can be performed more often than each 30 minutes. If replenishment is performed with 15 minutes intervals, the syringe rod 75 is only retracted halfway, etc.

In the embodiment according to FIG. 6, the introduction of glucose, i.e. 15 ml, is balanced by the removal of the same amount of peritoneal fluid, since the glucose bag 71 has a constant volume. This gives a ratio of 1:1 for UF removal and glucose addition, resulting in a net UF removal of zero.

Figure 7:
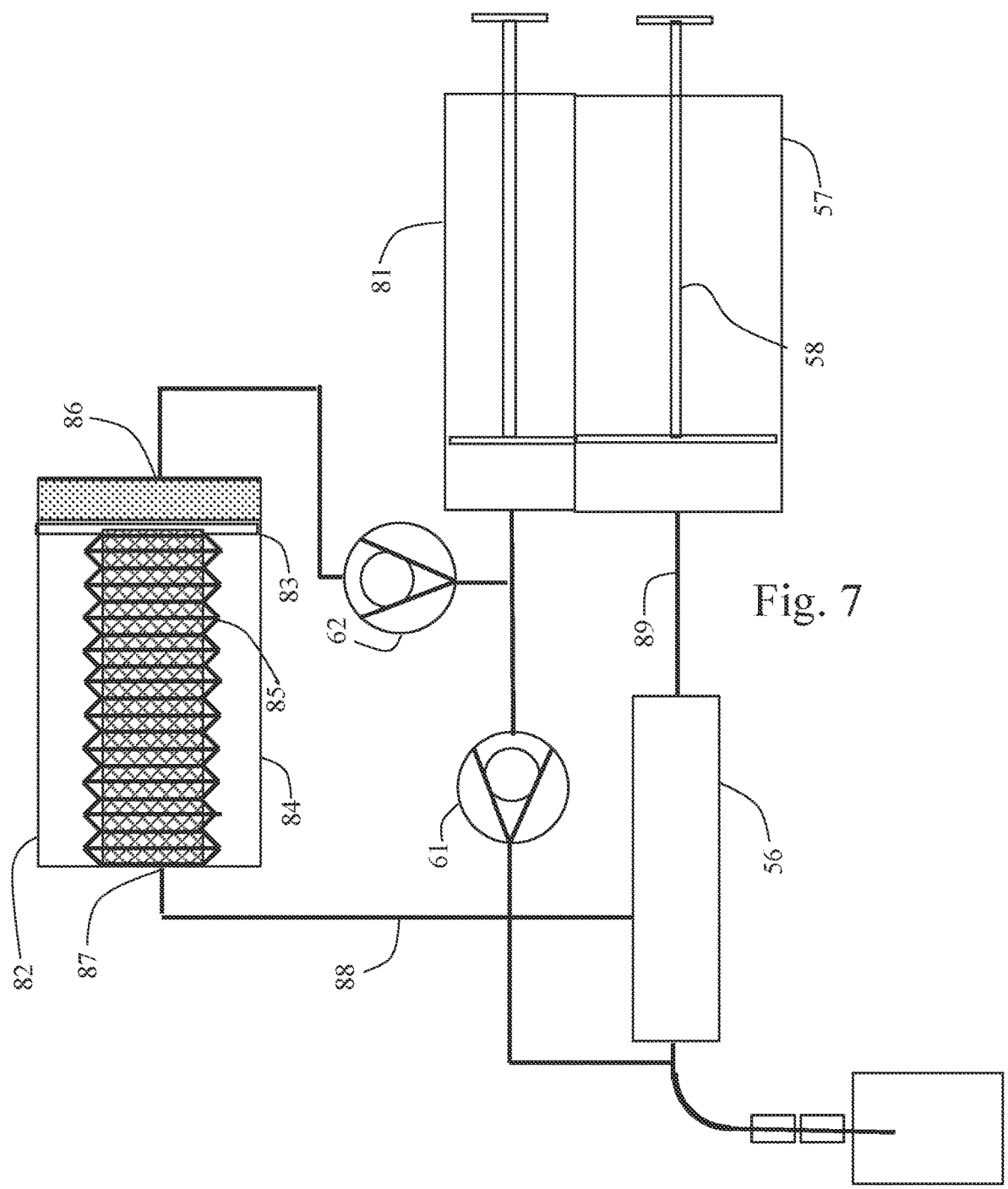
FIG. 7 is a schematic diagram of a third embodiment of an apparatus for providing an ultrafiltration fluid to a patient, comprising a dilution syringe and a UF syringe.

However, according to another embodiment, shown i FIG. 7, the ratio between the UF removal and the glucose infusion may be larger and constant. One example is that each infusion of 15 ml (0.5 ml/min) of glucose solution is balanced by a net removal of 60 ml (2 ml/min) of ultrafiltration fluid, or 75 ml (2.5 ml/min) if compensation for glucose infusion is included.

The apparatus according to FIG. 7 is similar to the apparatus according to FIG. 6. However, the second syringe 81 is larger and corresponds to a volume of 75 ml, while the first syringe 57 as before has a volume of 175 ml, or larger. In addition, the glucose bag is replaced by a combined glucose bag and UF bag. The combined bag 82 is arranges as a syringe having circular cross-section. A piston 83 is arranged to be moveable along the syringe 84. A bellow 85 is arranged to the left of the piston 83 and comprises glucose solution at 30%. The bellow is surrounded by air, which is vented to the atmosphere. The diameter of the piston 83 is the square root of five, i.e. 2.24 times the diameter of the bellow. Peritoneal fluid may be introduced to the right of the piston 83 via an inlet 86, resulting in that one fifth of the volume of UF fluid introduced to the right of the piston 83 is given off from the glucose bellow 85 via outlet 87. Thus, if 75 ml of UF fluid is introduced to the right of the piston, 15 ml of glucose solution is given off via outlet 87. Outlet 87 is connected to the mixing chamber by means of a line 88 in order to mix with fluid from the first syringe as described in connection with FIG. 6. The ratio between UF and glucose can be adjusted by changing the diameters of the bellow and syringe, while fine-tuning of the ratio is performed by adjustment of the glucose concentration.

Figure 8:
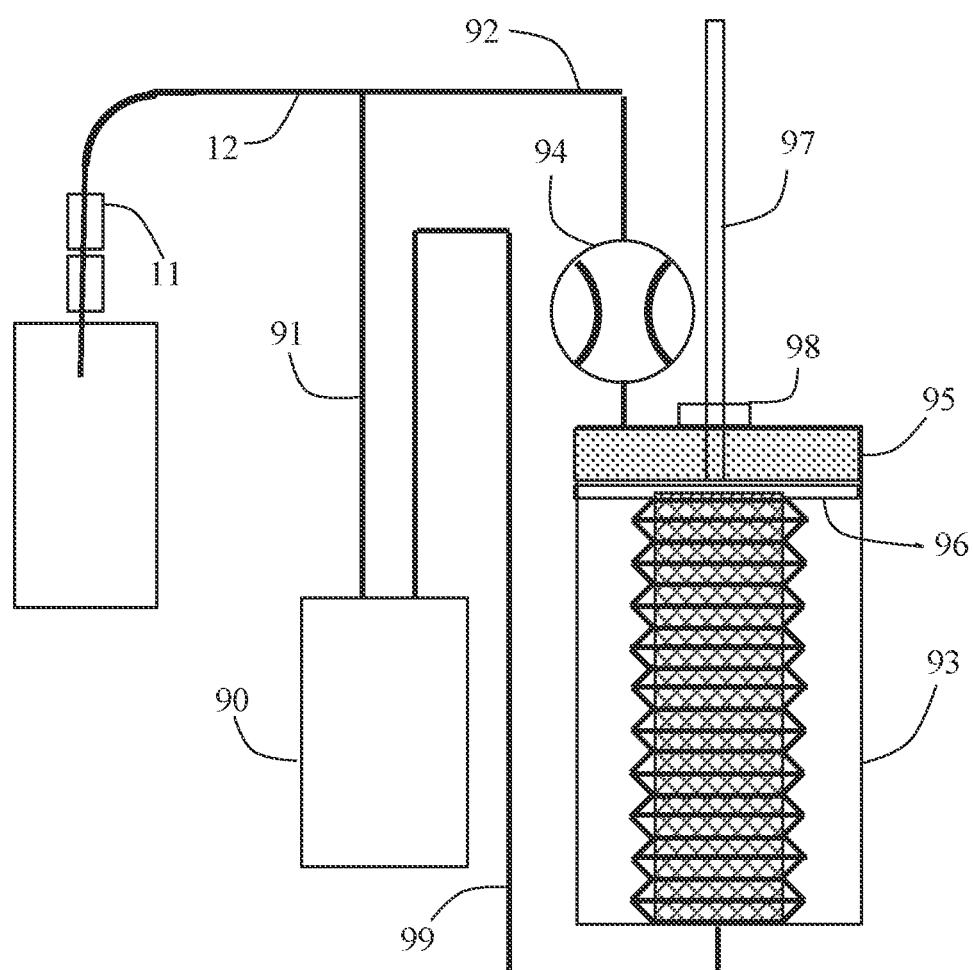
FIG. 8 is a schematic diagram of a fourth embodiment of an apparatus for providing an ultrafiltration fluid to a patient.

The piston 83 may include a grading as shown in FIG. 3 and/or a shoulder nut and piston rod as shown in FIG. 5, see also FIG. 8. In this manner, the infused glucose solution and removed UF may be controlled and monitored.

In the embodiment according to FIG. 7, no separate drain bag is required, except for the final drain.

FIG. 8 shows a further embodiment of the invention. It is noted that the peritoneal cavity always has a positive pressure, which may be 15 cm water pillar, or about 12 mmHg. This fact is used in the embodiment according to FIG. 8. The peritoneal cavity is connected to the patient connector 11 and patient line 12 as described above. The patient line 12 is connected to a flexible dilution bag 90 via a line 91 and to a combined glucose bag and UF bag 93 via a second line 92 and a restriction 94. Glucose solution is given off via a third line 99 to the dilution bag 90.

The dilution bag 90 and the combined bag 93 are both arranged at a low position, at or below the exit of the peritoneal catheter from the peritoneal cavity. Because of the hydrostatic pressure and/or because of the positive pressure inside the peritoneal cavity, peritoneal fluid will exit from the peritoneal cavity into the dilution bag 90 until it is full. The volume of the dilution bag is 190 ml or slightly larger. In addition, peritoneal fluid will pass to the upper compartment 95 delimited by a piston 96 of the combined bag 93 via a restriction 94. The combined bag 93 and the restriction 94 are arranged so that the flow through the restriction is at least 2.5 ml/min, for example 5 ml/min. The down-ward movement of the piston 96 is controlled by a syringe stem 97 and nut 98 as explained in connection with FIG. 5.

The operation is as follows:

Peritoneal fluid is given off from the peritoneal cavity to the patient line 12 and flows into the dilution bag 90 by gravity flow. Such a flow may be about 50 ml/min which means that it takes about 4 minutes to fill the dilution bag 90, if it has a volume of 200 ml. Simultaneously, there is a restricted flow of 5 ml/min into upper compartment 95, which results in a glucose solution flow of 1 ml/min into the dilution bag 90. When 15 ml has entered the dilution bag 90 after about 15 minutes, the flow stops because the nut 98 prevents further flow into the upper compartment 95. After another 15 minutes (totally 30 min), the patient squeezes the dilution bag 90, resulting in an increased pressure in the dilution bag 90 causing a flow of dilution fluid including 3% glucose to enter the peritoneal cavity. The fluid cannot flow from the dilution bag 90 to the upper compartment 95, since it is blocked by the nut 98 and stem 97. Fluid cannot escape back to the glucose bellow because of the hydrostatic ratio resulting in a five-fold increase of pressure in the glucose bellow.

When all fluid has been squeezed to the peritoneal cavity, the nut 98 is screwed up one revolution, allowing the piston to move down until 75 ml of UF fluid has again been entered in the upper compartment 95.

It is not important when the dilution bag is squeezed and how many times the dilution bag is squeezed during 30 minutes. Such squeezing can be done asynchronously. In order to ensure that the entered glucose concentration is below 3%, it is required that the fill rate of dilution bag 90 is more than about 12 times the fill rate of glucose. If the fill rate of glucose is 1 ml/min, as mentioned above, the fill rate of dilution bag 90 by peritoneal fluid (0.7% or up to 1.0%) should be at least about 14 ml/min (11.8 to 13.5) to yield a final concentration of less than 3%, which is normally achieved.

This method performs a more or less continuous removal of fluid from the peritoneal cavity balancing the ultrafiltration. Simultaneously, glucose is replenished in a constant ratio in relation to the ultrafiltration. It is believed that such a balance is beneficial to the patient.

The apparatus according to FIG. 8 may be further improved by arranging a small motor at the nut, which rotates the screw by two revolutions per hour. In this manner, a continuous and controlled removal of UF is obtained. The dilution bag 90 should be substantially filled between each squeezing (which may take some 5 minutes), otherwise it can be squeezed at any desired time.

The combination bag 93 may comprise a spring, which urges the piston 96 downwards in order to ensure that a flow is obtained at all times, independently of the exact position of the apparatus.

The dilution bag 90 may be of a bellow type similar to the glucose bellow and may also comprise a spring.

The apparatus may be modified for operation with a dual lumen catheter as shown in FIG. 10.

The apparatus may be modified in many respects to make the operation more easy, which is greatly appreciated by patients, who often may have difficulties to operate the apparatus properly.

Figure 9:
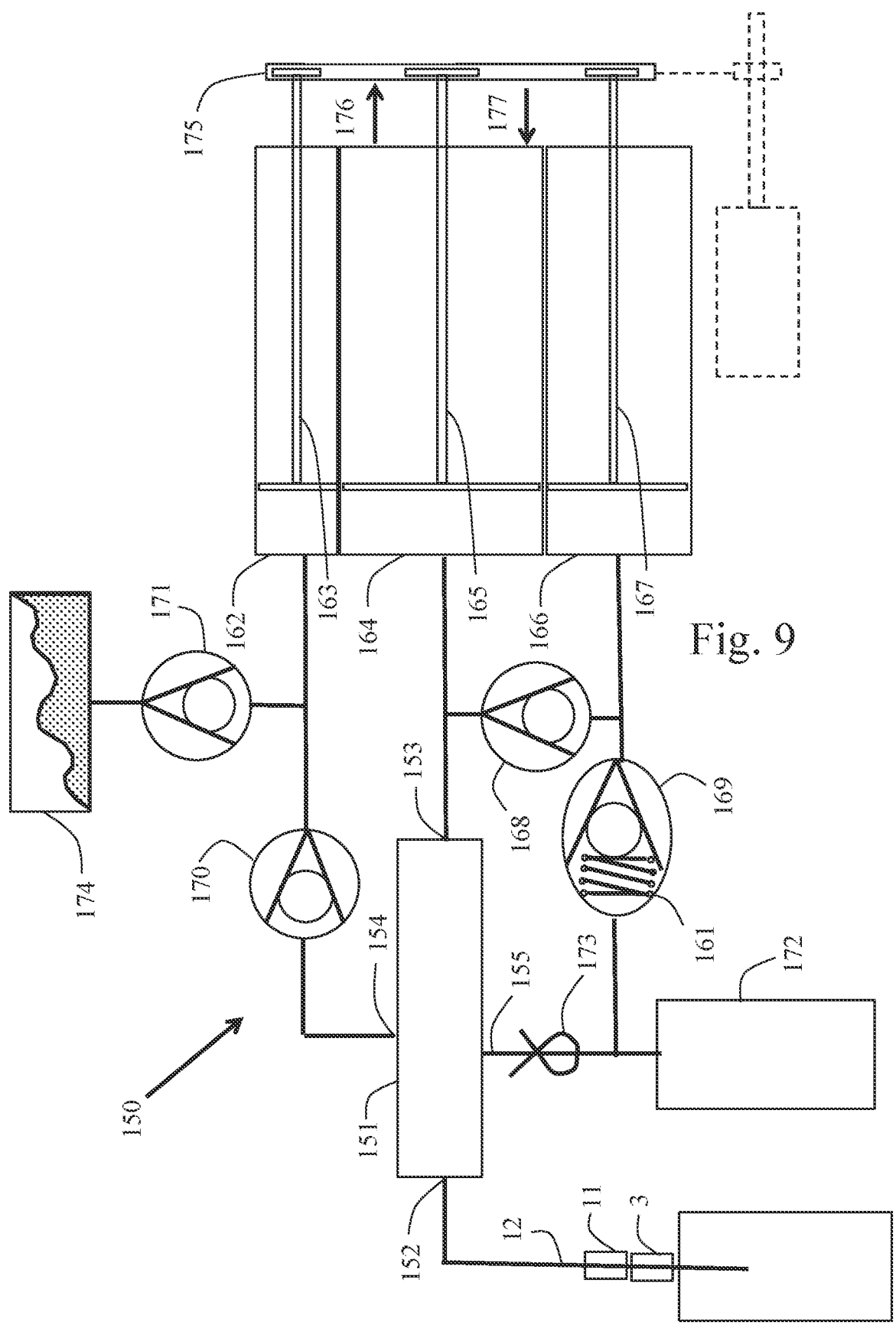
FIG. 9 is a schematic diagram of a fifth embodiment of an apparatus for providing an ultrafiltration fluid to a patient, comprising a dilution syringe and a UF syringe and a glucose syringe.

A further embodiment is shown in FIG. 9, wherein the manually operated valves are replaced by one-way valves permitting flow in only one direction and blocking flow in the other direction. In addition, there is arranged a third syringe for ultrafiltration.

The apparatus 150, as shown in FIG. 9, comprises the patient line 12 connected via patient connector 11 to the catheter connector 3 as in FIG. 3. The patient line 12 is connected to a first inlet/outlet 152 of a mixing chamber 151.

The apparatus comprises three syringes, a glucose syringe 162 comprising a glucose syringe stem 163, a dilution syringe 164 comprising a dilution syringe stem 165 and an ultrafiltration UF syringe 166 comprising an ultrafiltration UF syringe stem 167. The dilution syringe 164 is connected to a second inlet/outlet 153 of the mixing chamber 151. The UF syringe 166 is connected to the same second inlet/outlet 153 of the mixing chamber 151 via a one-way valve 168 which permits flow only in the direction towards the UF syringe 166. The UF syringe 166 is also connected to an ultrafiltration UF bag 172 via a one-way valve 169 permitting flow only from the syringe 166 to the UF bag 172. The UF bag 172 is also connected to a fourth inlet/outlet 155 of the mixing chamber 151 via a tube comprising a manually operated clamp 173. The glucose syringe 162 is connected to a third inlet/outlet 154 of the mixing chamber via a one-way valve 170 permitting flow only in the direction from the glucose syringe 162 to the mixing chamber 151. In addition, the glucose syringe 162 is connected to a glucose bag 174 via a one-way valve 171 permitting flow only in the direction from the glucose bag 174 to the glucose syringe 162. The three syringe stems 163, 165 and 167 are interconnected by a syringe rod 175 for movement in unison. The syringe stems can be separated from the syringe rod 175 for separate movements.

The operation of the apparatus 150 is as follows:

In a first step, the interconnection stem 175 is pulled to the right in FIG. 9, according to arrow 176. The glucose syringe 162 is filled with 15 ml of glucose solution. The dilution syringe 164 and the UF syringe 166 are filled with 175 ml and 75 ml of peritoneal fluid taken from the peritoneal cavity via the patient connector 11, patient tube 12 and mixing chamber 151.

When the syringe rod 175 has reached its end position, the direction of movement is reversed according to arrow 177. Now, the contents (75 ml) of UF syringe 166 is transferred to the UF bag 172 via one-way valve 169, since the one-way valve 168 blocks any other route. Simultaneously, the contents (15 ml) of the glucose syringe 162 is delivered to the mixing chamber 151 via one-way valve 170 and inlet 154, which may be arranged in the side of the mixing chamber as shown in FIG. 9, and the contents (175 ml) of the dilution syringe 164 is delivered to the second inlet/outlet 153 of the mixing chamber, which may be arranged at the end of the mixing chamber as shown in FIG. 9. Now, the flow of glucose via inlet 154 is mixed with the flow of peritoneal fluid via inlet 153 in a ratio determined by the size of the respective syringes 162 and 164, which is 15:175. Finally, the mixture of peritoneal fluid and glucose is delivered to the patient via the first inlet/outlet 152 of the mixing chamber. The concentration of glucose in said solution is less than but close to about 3%.

The glucose bag 174 may be provided with a grading indicating how much glucose has been used similar to the embodiment shown in FIG. 3. If the treatment time is 10 hours and replenishments are performed each 30 minutes, the grading or scale may have 20 lines. In this manner, the patient can determine that he has not missed any replenishment cycle by comparing the grading scale with the present time at his watch.

It is not necessary to make a full movement of the connection bar 175. If replenishments are performed more often, for example after 15 minutes, only half of the volumes are used. In this case, the connection bar 175 is pulled only half the way to the right. By reading the grading and comparing with the present time, the patient can determine the exact amount to use at any give time. For example, if the replenishment is performed after 20 minutes, the patient pulls the connection bar 175 until the grading shows the correct amount. On the other hand, if the replenishment is performed after 40 minutes, a complete pulling of the connection rod 175 is not sufficient for reaching the grading scale line corresponding to the actual time. In this case, the patient first performs a complete pull followed by a complete push of the connection rod 175, where after the patient performs a non-complete second pull and push sequence so that the glucose indication becomes opposite the correct grading line corresponding to the actual time. This, relieves the patient from performing replenishments exactly each 30 minutes, but the replenishments can be done more asynchronously, which is greatly appreciated by the patient.

It is noted that if the UF bag 172 is arranged in a low position, peritoneal fluid may pass via the one-way valves 168 and 169 to the UF bag 172 in an uncontrolled manner. In order to avoid such unintended flow, the second one-way valve 169 may be arranged as a pressure relieve valve as shown in FIG. 9, which allows flow only if the pressure exceeds a pressure determined by a spring 161 and prevents flow in the opposite direction. Such pressure may be 100 mmHg, which is sufficient for preventing any undesired flow.

The above embodiments of the apparatus are arranged for being operated manually by the patient, whereby no battery is required since there is no device driven by a battery. Thus, the apparatus is very safe and easy to operate and is only dependent on the patient for correct operation. The apparatus comprises means which will aid the patient in correct operation.

The apparatus is intended to be used during daytime, when the patient is awake for manual operation of the apparatus.

However, the apparatus is easily adaptable for night operation. The patient is anyhow immobile in his bed during sleep in the night. Thus, there may be arranged electric devices exerting forces on the syringe stems and electric devices switching the valves, in each of the different embodiments.

In the embodiment according to FIG. 9, an electric motor may be arranged to move the syringe rod 175 according to arrows 176 and 177 as shown by broken lines. Alternatively, a pneumatic or hydraulic actuator may move the syringe rod 175 according to arrows 176 and 177, driven by a pneumatic or hydraulic power source.

In the embodiment according to FIG. 3, there is arranged an electric motor driving the syringe stem according to arrows 18 and 19. In addition, there is arranged actuators, which switches the valves 29 and 29 appropriately. In the embodiment according to FIG. 5, there is additionally two electric motors, which appropriately rotate the nuts 38, 39 or alternatively the syringe stems 36, 37. In the embodiment according to FIG. 7, there is only needed one electric actuator which drives the syringe stems in and out of the syringes. In the embodiment according to FIG. 8, there is needed an electric motor rotating the nut 98 and an actuator squeezing and releasing the bag 90 with regular intervals. Similar arrangements are made in the other embodiments.

The electric motors and actuators may be arranged to be attached to the apparatus by releasable devices, so that the apparatus may be put in a dock arrangement wherein the apparatus is connected to the motors and actuators for automatic operation and the apparatus may be removed from the dock arrangement for manual operation.

If the patient wants to take a rest or siesta during daytime, the patient may arrange the apparatus in the dock arrangement for automatic operation during the rest or siesta, and then release the apparatus from the dock arrangement after the siesta for manual operation.

The apparatus may be arranged for operation in connection with a double lumen catheter.

The apparatus should be provided with arrangements for priming. In the embodiment shown in FIG. 6, the drain bag 55 may initially be provided with 200 ml of priming solution. During a priming step, the valve 51 is arranged in the position shown in broken lines, and the priming solution is delivered to the syringes 57, 59 by pulling the syringe rod 75 until 190 ml of fluid has been entered into the two syringes. Next, the syringe rod 75 is pushed whereby the fluid in the second syringe 59 is passed to the glucose bag 71 and glucose concentrate is passed via line 78 to the mixing chamber 56 and further back to the drain bag 55 together with the contents of the first syringe 57. The priming step can be repeated several times.

Similar priming steps may be arranged in the other embodiments.

The patient having congestive heart failure may also have low blood pressure, which may compromise the operation of the kidney. The kidney may require support in removal of excess water, since the urine production is smaller than normal. However, the excretion of metabolic waste products, such as urea and creatinine, may normally be sufficient.

However, because of the low urine volume, an insufficient removal of sodium may prevail. Thus, the fluid used in these embodiments may be modified by reducing the sodium concentration, which results in removal of sodium, in addition to removal of UF fluid as described above. If the removal of potassium of the kidney is too low, a lowering of the potassium concentration in the initial fresh peritoneal fluid may be appropriate, or even elimination of potassium from the fluid. However, the body is sensitive to low potassium concentration in blood, and a lowering or removal of the potassium concentration should be carefully supervised by a doctor.

The patient having congestive heart failure may have a compromised blood pressure as indicated above. Such blood pressure may result in partial withdrawal of capillaries in the peritoneal membrane and adjacent tissue, resulting in less exchange of substances between the fluid in the peritoneal cavity and the blood. The result is less ultrafiltration. However, the continuous supply of glucose is expected to reduce any tendency for the capillaries to withdraw, since the body is not exposed to transient conditions. Thus, the gentle and continuous replenishment of glucose is expected to be of great importance for sensitive patients.

The peritoneal membrane is sensitive to excessive exposure to glucose, which may result in peritoneal pain and peritonitis and tissue alterations. A gentle exposure of the peritoneal membrane to glucose may counteract such problems. Accordingly, the initial instillation of fluid into the peritoneal cavity may take place with a low concentration of glucose, or even zero glucose. Then, the concentration of glucose is increased slowly.

Due to the fact that a replenishment of glucose is made intermittently with short intervals, a low concentration of glucose may be used and still a desired ultrafiltration may be achieved. This is advantageous for avoiding pain and peritonitis as well for maintaining the ultrafiltration function of the peritoneal membrane.

If the patient during the treatment is exposed to hypotension or other problems, resulting in withdrawal of capillaries in the peritoneal membrane, this is manifested as a lowering of the ultrafiltration and a lowering of glucose absorption. The lowered glucose absorption may be monitored by a glucose sensor and may result in an alarm to the patient and/or supervising persons.

The glucose bag may comprise glucose at a concentration of 10%, 20%, 30%, 40% or 50%. The volume of peritoneal fluid entered into the peritoneal cavity may be about 1 to 3 liter, for example 1.5 liter. The peritoneal fluid may comprise ions of sodium 132 mM (mmole/liter), potassium 2 mM, calcium 2.5 mM, magnesium 0.5 mM, chloride 95 mM and lactate 40 mM. Lactate may be replaced by acetate or bicarbonate.

If sodium ions should be removed, the sodium ion concentration may be lowered to 95 mM or lower. The potassium concentration may be lowered or removed.

The glucose bag may comprise some sodium or no sodium, in order to influence upon the sodium balance.

The osmotic agent mentioned above is glucose, which has been shown to be working well for ultrafiltration of a peritoneal dialysis patient. However, other osmotic agents may be used such as Icodextrin, which is a glucose polymer.

In the claims, the term "comprises/comprising" does not exclude the presence of other elements or steps. Furthermore, although individually listed, a plurality of means, elements or method steps may be implemented by e.g. a single unit. Additionally, although individual features may be included in different claims or embodiments, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

Although the present invention has been described above with reference to specific embodiment and experiments, it is not intended to be limited to the specific form set forth herein. Rather, the invention is limited only by the accompanying claims and, other embodiments than those specified above are equally possible within the scope of these appended claims.

The invention claimed is:

1. An apparatus for performing ultrafiltration of a patient having a peritoneal fluid installed in a peritoneal cavity, comprising:

a patient line comprising a patient connector for connection to a peritoneal catheter connector for access to the peritoneal fluid of the peritoneal cavity of the patient;

a dilution receptacle connected to the patient line for removal and return of a dilution volume of the peritoneal fluid from and to the peritoneal cavity, wherein the dilution receptacle is a syringe having a retractable piston;

an ultrafiltration receptacle for receipt of an ultrafiltration volume of the peritoneal fluid;

a glucose receptacle configured to contain glucose concentrate to be added to the dilution volume;

a first valve arranged for connection of said syringe with said patient tube in a first position, and for connection of said syringe with a second valve in a second position;

said second valve being arranged for connection of said first valve to the ultrafiltration receptacle in a first position, and for connection of said first valve to said glucose receptacle in a second position;

a metering device configured to meter an amount of glucose concentrate which is positively proportional to said ultrafiltration volume removed from the patient and is added to said dilution volume at each cycle;

whereby glucose is replenished intermittently to said peritoneal fluid of said peritoneal cavity.

2. The apparatus according to claim 1, wherein the ultrafiltration receptacle is arranged as a syringe comprising a syringe stem attached to a corresponding piston and a nut or shoulder arranged moveable along the syringe stem for limiting the movements of the pistons of each syringe.

3. The apparatus according to claim 1,
wherein the glucose receptacle comprises an enclosure having a constant volume, and a partition wall dividing the enclosure into two compartments, a first of which comprising glucose concentrate and a second of which comprising peritoneal fluid, and wherein introduction of peritoneal fluid inside the second compartment displaces an equal volume of glucose concentrate out of the first compartment.

4. The apparatus according to claim 1, wherein said ultrafiltration receptacle is connected to the patient line via a one-way valve and further connected to a combination bag via a second one-way valve, wherein said combination bag comprises a first compartment for ultrafiltration fluid and a second compartment comprising glucose concentrate, whereby inflow of ultrafiltration fluid in said first compartment results in an outflow of glucose concentrate, wherein the ratio between inflow and outflow is constant and larger than one.

5. A method of performing ultrafiltration of a patient having a peritoneal fluid installed in a peritoneal cavity, comprising:

removal of an ultrafiltration volume of the peritoneal fluid from the peritoneal cavity of the patient;

removal of a dilution volume of the peritoneal fluid from the peritoneal cavity of the patient;

addition of glucose concentrate to the dilution volume, wherein an amount of glucose concentrate is added, which is positively proportional to said ultrafiltration volume removed from the patient at each cycle;

returning the dilution volume of peritoneal fluid with added glucose concentrate to the peritoneal cavity of the patient;

repeating said method steps with a time interval of less than 60 minutes.

6. The method according to claim 5, wherein the method steps are repeated with a time interval of between 10 minutes and 60 minutes.

7. An apparatus for performing ultrafiltration of a patient having a peritoneal fluid installed in a peritoneal cavity, comprising:

a patient line comprising a patient connector for connection to a peritoneal catheter connector for access to said peritoneal fluid of the peritoneal cavity of the patient;

a dilution receptacle connected to said patient line for removal and return of a dilution volume of the peritoneal fluid from and to the peritoneal cavity, an ultrafiltration receptacle for receipt of an ultrafiltration volume of the peritoneal fluid;

a glucose receptacle configured to contain glucose concentrate to be added to the dilution volume;

a valve arrangement for selectable connection of said dilution receptacle with said glucose receptacle and with said patient tube;

wherein an amount of glucose concentrate which is positively proportional to said ultrafiltration volume removed from the patient is added to said dilution volume;

whereby glucose is replenished intermittently to said peritoneal fluid of said peritoneal cavity.

8. The apparatus according to claim 7, wherein the dilution receptacle is a syringe having a retractable piston and a syringe stem for operation of the piston, and wherein the apparatus further comprises:

a first valve, which is arranged for connection of said syringe with said patient tube in a first position, and for connection of said syringe with a second valve in a second position; wherein the second valve being arranged for connection of the first valve to the ultrafiltration receptacle in a first position, and for connection of the first valve to the glucose receptacle in a second position.

9. The apparatus according to claim 7, wherein the glucose receptacle and the ultrafiltration receptacle are arranged as syringes each comprising a syringe stem attached to a corresponding piston and a nut or shoulder arranged moveable along the syringe stem for limiting the movements of the pistons inside of each syringe.

10. The apparatus according to claim 7, wherein the glucose receptacle comprises an enclosure having a constant volume, and a partition wall dividing the enclosure into two compartments, a first of which comprising glucose concentrate and a second of which comprising peritoneal fluid, and wherein introduction of peritoneal fluid inside the second compartment displaces an equal volume of glucose concentrate out of the first compartment.

11. The apparatus according to claim 7, wherein said ultrafiltration receptacle is connected to the patient line via a first one-way valve and further being connected to a combination bag via a second one-way valve, wherein said combination bag comprises a first compartment for ultrafiltration fluid and a second compartment comprising glucose concentrate, whereby inflow of ultrafiltration fluid in said first compartment results in an outflow of glucose concentrate, wherein the ratio between inflow and outflow is constant and larger than one.

12. The apparatus according to claim 7, wherein said valve arrangement comprises at least one one-way valve.

* * * * *